(12) United States Patent
Wang et al.

(10) Patent No.: US 7,781,588 B1
(45) Date of Patent: Aug. 24, 2010

(54) ACRIDAN MONOMERS AND POLYMERS

(75) Inventors: Hailiang Wang, Camarillo, CA (US);
Zhensheng Zhang, Santa Barbara, CA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1279 days.

(21) Appl. No.: 11/303,708

(22) Filed: Dec. 16, 2005

Related U.S. Application Data

(60) Provisional application No. 60/640,599, filed on Dec. 30, 2004, provisional application No. 60/694,882, filed on Jun. 28, 2005.

(51) Int. Cl.
*C07D 219/00* (2006.01)
*C07D 219/08* (2006.01)
(52) U.S. Cl. ...................... 546/102; 546/104
(58) Field of Classification Search .................. 514/250; 546/102, 104
See application file for complete search history.

(56) References Cited

U.S. PATENT DOCUMENTS 5,624,929 A * 4/1997 Mylari et al. ................ 514/256
6,303,238 B1 10/2001 Thompson et al. .......... 428/690
2001/0019782 A1 9/2001 Igarashi et al. .............. 428/690

FOREIGN PATENT DOCUMENTS

| EP | 1 191 612 A2 | 3/2002 |
|---|---|---|
| EP | 1 191 614 A2 | 3/2002 |
| WO | WO 00/70655 | 11/2000 |
| WO | WO 01/41512 A1 | 6/2001 |
| WO | WO 02/02714 A2 | 1/2002 |
| WO | WO 02/15645 A1 | 2/2002 |

OTHER PUBLICATIONS

Molock et. al., Journal of Heterocyclic Chemistry, 1983, Wiley Science, vol. 20, issue 1, pp. 109-112.*
Gustafsson, G. et al., "Flexible Light-Emitting Diodes made from Soluble Conducting Polymer", *Nature*, 1992, 357, 477-479.
O'Brien, D.F. et al., "Electrophosphoresence from a Doped Polymer Light Emitting Diode", *Synthetic Metals*, 2001, 116(1-3), 379-383.
Campbell, I.H. et al., "Excitation Transfer Processes in a phosphor-doped poly (p-phenylene vinylene) Light-Emitting Diode" *Physical Review B*, 65, 085210-1-085210-8, (2002).
Othmer, K., *Encyclopedia of Chemical Technology*, 1996, 18 (4$^{th}$ Ed), 837-860.
Markus, J., *Electronics and Nucleonics Dictionary*, 1966, 3$^{rd}$ Edition, 470, 471, 476.

* cited by examiner

*Primary Examiner*—Sreeni Padmanabhan
*Assistant Examiner*—Sarah Pihonak
(74) *Attorney, Agent, or Firm*—Woodcock Washburn LLP

(57) ABSTRACT

Acridian monomers and polymers are described, as well as their use in organic electronic devices, and materials and methods for fabrication of the same.

5 Claims, 2 Drawing Sheets

ACRIDAN MONOMERS AND POLYMERS

CROSS REFERENCE

This application claims the benefit of priority under 35 U.S.C. §119(e) from provisional U.S. Application Ser. Nos. 60/640,599, filed Dec. 30, 2004, and 60/694,882, filed Jun. 28, 2005, the disclosures of which are each incorporated herein by reference in their entireties.

FIELD

This disclosure relates generally to acridian monomers and polymers, their use in organic electronic devices, and materials and methods for fabrication of the same.

BACKGROUND

Organic electronic devices convert electrical energy into radiation, detect signals through electronic processes, convert radiation into electrical energy, or include one or more organic semiconductor layers. Most organic electronic devices contain charge transport materials to facilitate migration of positive or negative charges through the organic device with relative efficiency and small loss of charges.

Thus, what is needed are charge transport materials.

SUMMARY

In one embodiment, acridian monomers are provided, as well as polymers therefrom and methods for making the same, and devices and sub-assemblies including the same.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
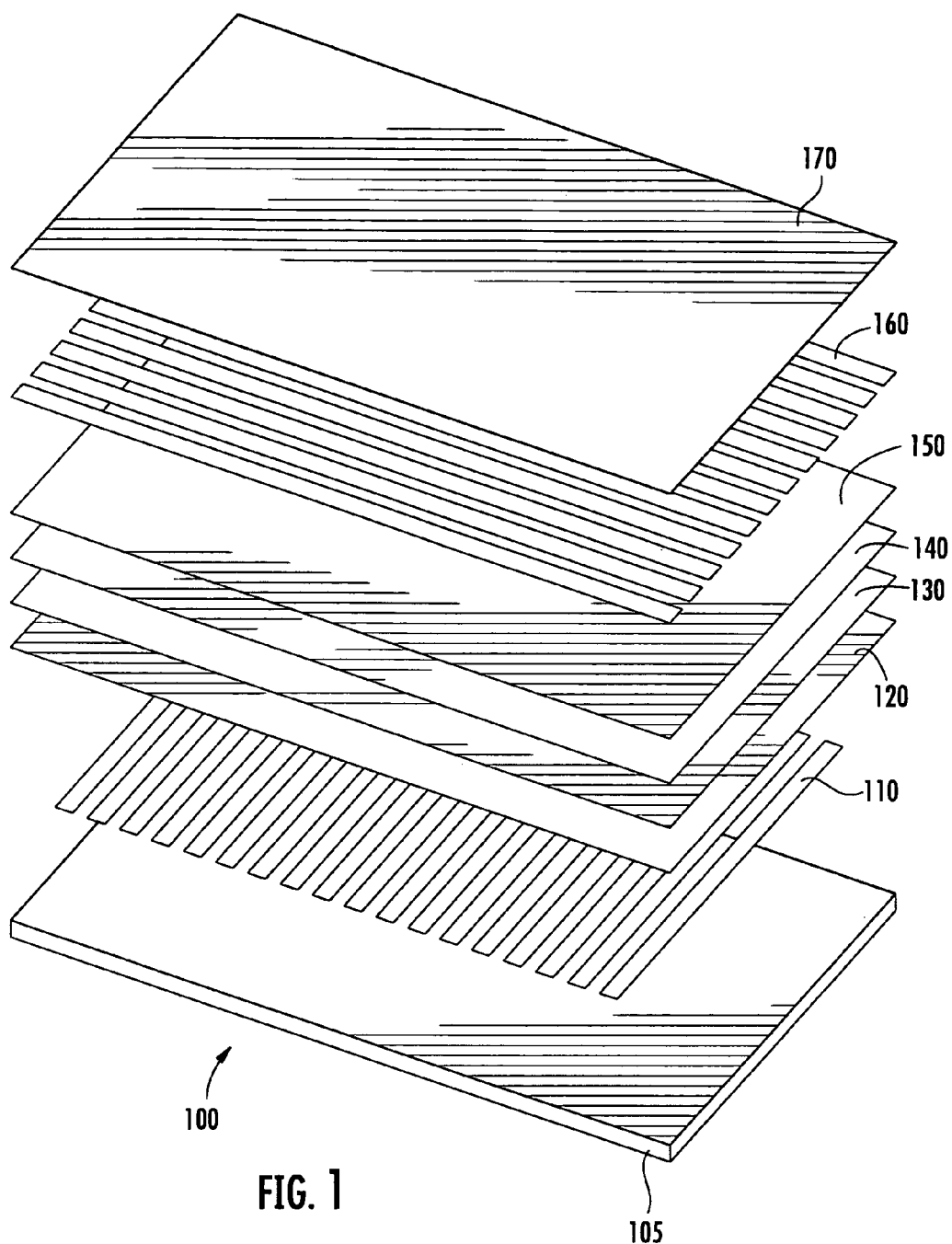
FIG. 1 is a schematic diagram of an organic electronic device.

The figures are provided by way of example and are not intended to limit the invention. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

In one embodiment, compounds are provided having formula I:

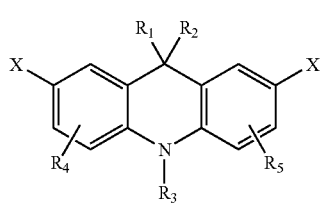

I wherein:

$R_1$, $R_2$, $R_3$, $R_4$, and $R_5$ are each, independently, H, alkyl, alkenyl, alkynyl, heteroalkyl, heteroalkenyl, heteroalkynyl, or aryl;

X is, independently, Br, I, —COOH, or —$C_6H_4$—COOH.

In one embodiment, when $R_4$ and $R_5$ are both H, at least one of $R_1$-$R_3$ is other than H.

In one embodiment, at least one of $R_1$, $R_2$, $R_3$, $R_4$, and $R_5$ is further substituted with halogen, amino, cyano, nitro, alkyl, alkoxy, alkylamino, or alkylthio.

In one embodiment, $R_1$ and $R_2$ are both alkyl.

In one embodiment, $R_3$ is aryl. In one embodiment, $R_3$ is phenyl.

In one embodiment, $R_3$ is alkyl.

In one embodiment, acridian monomers of formula I are those wherein:

$R_1$, $R_2$, $R_3$, $R_4$, and $R_5$ are each independently —H or substituted or unsubstituted $C_1$-$C_{100}$ alkyl, substituted or unsubstituted $C_2$-$C_{100}$ alkenyl, or substituted or unsubstituted $C_2$-$C_{100}$ alkynyl, wherein substituents are selected from halogen, amino, cyano, nitro, alkyl, alkoxy, alkylamino, alkylthio, and wherein one or more methylene units of the $C_1$-$C_{100}$ alkyl, $C_2$-$C_{100}$ alkenyl, or $C_2$-$C_{100}$ alkynyl are optionally replaced with —O—, —S—, or NR', wherein R' is a $C_5$-$C_{14}$ saturated cyclic hydrocarbon or aromatic hydrocarbon, or $R_1$, $R_2$, $R_3$, $R_4$, and $R_5$ are each independently substituted or unsubstituted $C_5$-$C_{14}$ aryl, wherein substituents are selected from halogen, amino, cyano, nitro, alkyl, alkoxy, alkylamino, alkylthio, with the proviso that when $R_4$ and $R_5$ are both —H, at least one of $R_1$-$R_3$ is not —H.

Additional exemplary acridan monomers are set forth below:

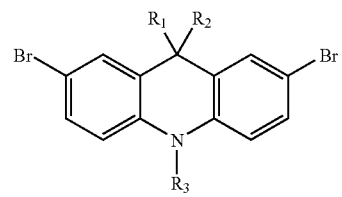

1) $R_1$, $R_2$=$C_4H_9$; $R_3$=H

2) $R_1$, $R_2$=$C_4H_9$, $R_3$=$C_6H_{13}$

3) $R_1$, $R_2$=$C_4H_9$; $R_3$=$C_6H_{13}$

4) $R_1$, $R_2$=$C_4H_9$; $R_3$=tert-butyl-benzyl.

In one embodiment, compositions are provided comprising the above-described compounds and at least one solvent, processing aid, charge transporting material, or charge blocking material. These compositions can be in any form, including, but not limited to solvents, emulsions, and colloidal dispersions.

A variety of syntheses are contemplated for preparation of acridan monomers. An exemplary synthetic route is set forth below in Scheme 1.

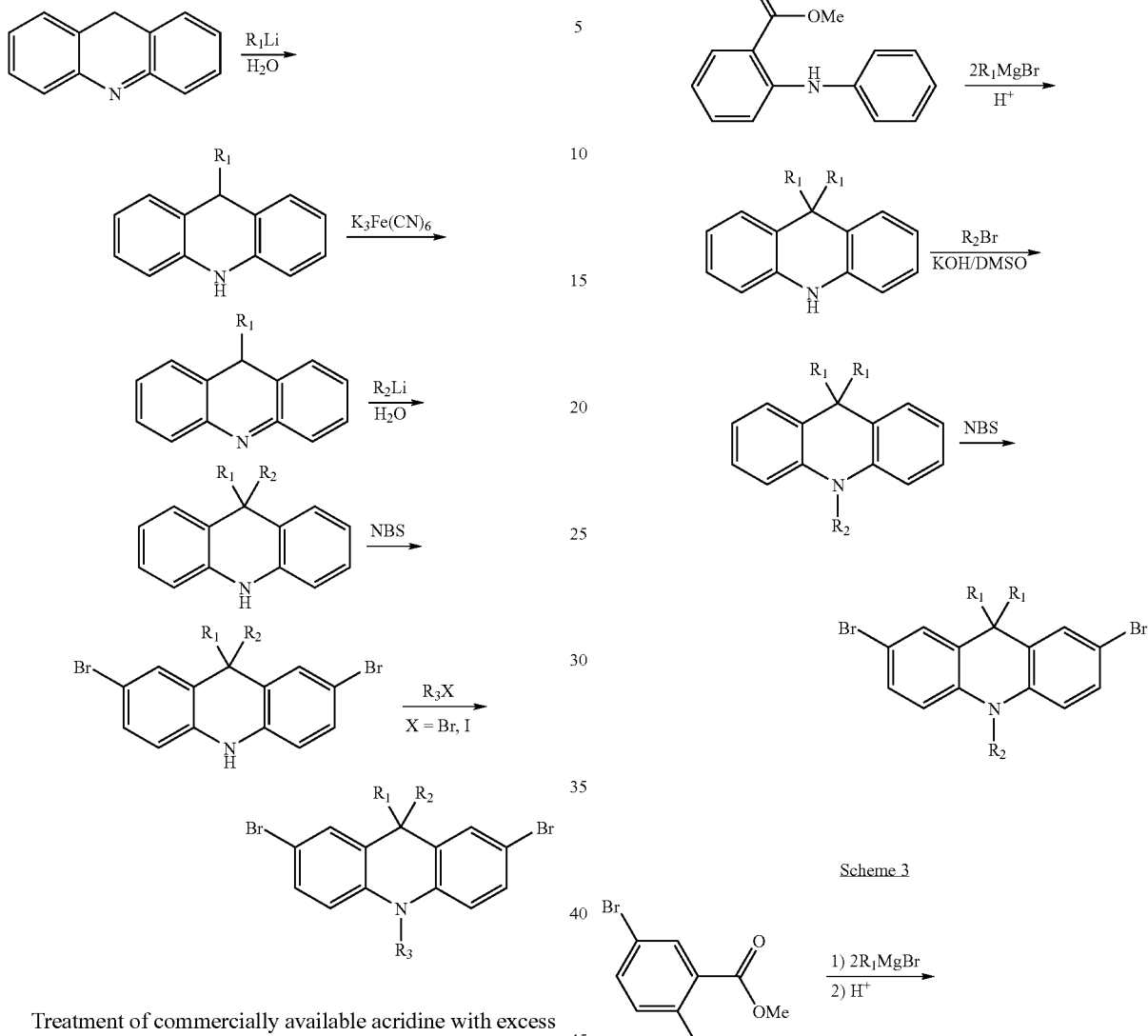

Treatment of commercially available acridine with excess organolithium followed by water quenching provides 9-($R_1$)-acridan. 9-($R_1$)-acridan is converted to the corresponding acridine via oxidation with $K_3Fe(CN)_6$. Reaction of 9-($R_1$)-acridine with a second equivalent organolithium followed by water quenching provides the dialkyl acridan 9,9-($R_1$,$R_2$)-acridan. Controlled bromination with N-bromosuccinimide (NBS) followed by amine alkylation with $R_3X$ (X=Br, I) provides an exemplary acridan monomer.

Alternative synthetic routes to acridan monomers are set forth below in Schemes 2-4.

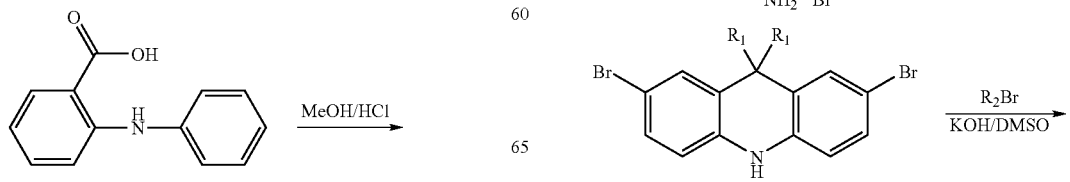

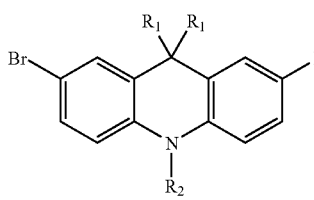

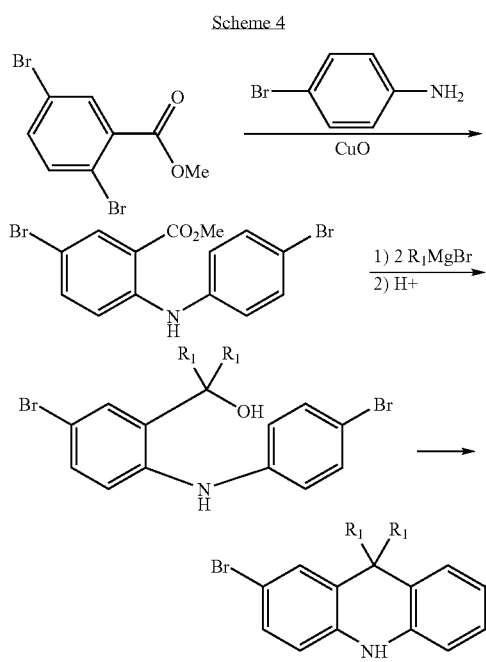

In other embodiments, there are provided compositions comprising the compound according to the structure I and at least one solvent, processing aid, charge transporting material, or charge blocking material. These compositions can be in any form, including but not limited to solvents, emulsions, and colloidal dispersions.

In one embodiment, oligomers made from the monomers of structure I are provided.

In one embodiment, monomers of structure I are used to make homopolymers or random, block, graft, or alternating copolymers.

In one embodiment, there are provided polymers having the structure II:

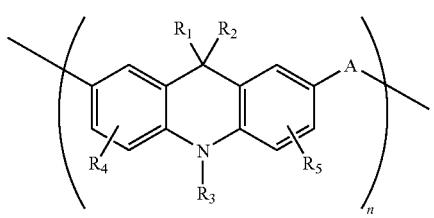

II wherein:

$R_1$, $R_2$, $R_3$, $R_4$, and $R_5$ are each independently —H or substituted or unsubstituted $C_1$-$C_{100}$ alkyl, substituted or unsubstituted $C_2$-$C_{100}$ alkenyl, or substituted or unsubstituted $C_2$-$C_{100}$ alkynyl, wherein substituents are selected from halogen, amino, cyano, nitro, alkyl, alkoxy, alkylamino, alkylthio, and wherein one or more methylene units of the $C_1$-$C_{100}$ alkyl, $C_2$-$C_{100}$ alkenyl, or $C_2$-$C_{100}$ alkynyl are optionally replaced with —O—, —S—, or NR', wherein R' is a $C_5$-$C_{14}$ saturated cyclic hydrocarbon or aromatic hydrocarbon, or $R_1$, $R_2$, $R_3$, $R_4$, and $R_5$ are each independently substituted or unsubstituted $C_5$-$C_{14}$ aryl, wherein substituents are selected from halogen, amino, cyano, nitro, alkyl, alkoxy, alkylamino, alkylthio, with the proviso that when $R_4$ and $R_5$ are both —H, at least one of $R_1$-$R_3$ is not —H, A is a substituted or unsubstituted aromatic or heteroaromatic hydrocarbon moiety, wherein substituents are selected from halogen, amino, cyano, nitro, alkyl, alkoxy, alkylamino, or alkylthio, and n is at least 5.

In some embodiments, the polymer is a homopolymer. In other embodiments, the polymer is a copolymer, i.e., having two or more different monomeric units, each monomeric unit according to the structure II, as provided above.

In one embodiment, the polymer includes fluorene units. In one embodiment, the fluorene is a 9,9-($C_1$-$C_{10}$-dialkyl)fluorene.

In one embodiment, polymers are synthesized using a modified Suzuki coupling procedure as set forth in Scheme 5.

Scheme 5

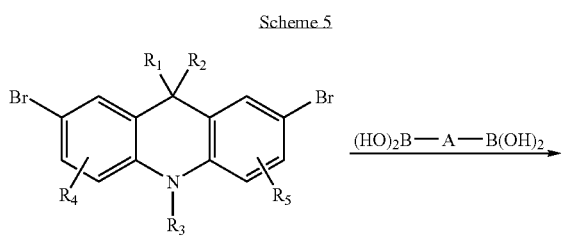

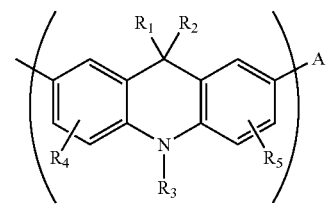

In a typical polymerization reaction, equimolar amounts of acridan monomer and fluorine monomer are dissolved in a solvent system such as THF (tetrahydrofuran/K2CO3 (aq.)), with (PPh$_3$)$_4$Pd as a catalyst and a trace amount of benzenetriethylammonium chloride as a phase transfer catalyst. The resulting polymer is readily soluble in a variety of common organic solvents, such as THF, toluene, and the like. The molecular weights of the acridan polymers range from about 1000 up to about 1,000,000.

An exemplary polymer wherein A is 9,9-dialkylfluorene is set forth below:

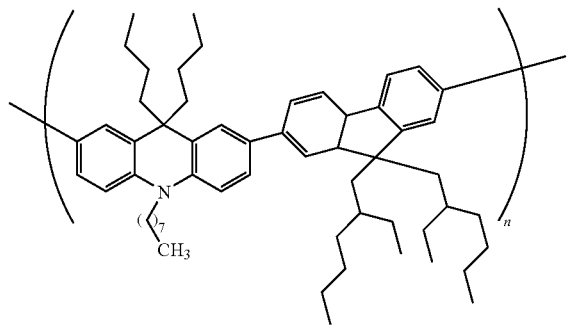

In certain other embodiments, the polymer is an acridan homopolymer, i.e., the polymer is composed entirely of repeating acridan monomer units. An example of such a polymer is set forth below:

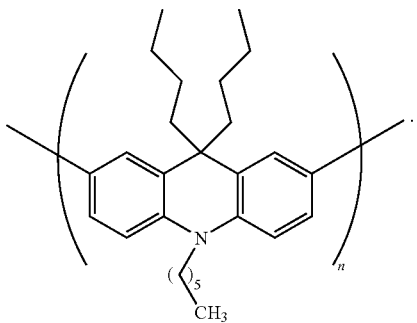

Also provided are compositions comprising the polymer according to the structure II and at least one solvent, processing aid, charge transporting material, or charge blocking material.

In further embodiments, there are provided charge transport layers comprising acridian polymers, and organic electronic devices containing the same.

Device

Referring to FIG. 1, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8, 10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in *Flexible Light-Emitting Diodes Made From Soluble Conducting Polymer, Nature* 1992, 357, 477-479. At least one of the anode and cathode should be at least partially transparent to allow the generated light to be observed.

An optional buffer layer 120, such as hole transport materials, may be deposited over the anode layer 110, the latter being sometimes referred to as the "hole-injecting contact layer." Examples of hole transport materials suitable for use as the layer 120 have been summarized, for example, in Kirk Othmer, Encyclopedia of Chemical Technology, Vol. 18, 837-860 (4$^{th}$ ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4,4'-diamine (TPD), 1,1 bis[(di-4-tolylamino)phenyl]cyclohexane (TAPC), N,N' bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N-diphenylaminostyrene (TPS), p (diethylamino)benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino) styryl]-5-[p-(diethylamino)phenyl]pyrazoline (PPR or DEASP), 1,2 trans-bis(9H-carbazol-9-yl)cyclobutane (DCZB), N,N,N',N' tetrakis(4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the buffer layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in *Synth. Met.* 2001, 116 (1-3), 379-383, and Campbell et al., in Phys. Rev. B, Vol. 65 085210.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a layer (not shown) between the anode 110 and hole transport layer 120 to facilitate positive charge transport and/or bandgap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition. Devices may also be sub-assembled into separate articles of manufacture that can then be combined to form the device.

DEFINITIONS

The use of "a" or "an" are employed to describe elements and components of the invention. This is done merely for convenience and to give a general sense of the invention. This description should be read to include one or at least one and the singular also includes the plural unless it is obvious that it is meant otherwise.

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

EXAMPLES

The concepts described herein will be further described in the following examples, which do not limit the scope of the invention described in the claims.

Example 1

This Example describes a synthetic route to an acridan monomer, 2,7-dibromo-9,9-dibutylacridan.

Part A: Preparation of 9-butylacridine

To an ice-cooled solution of acridine (24.8 g, 0.139 mol) and TMEDA (N,N,N',N'-tetramethylethylenediamine) (5.0 ml, 0.034 mol) in THF (160 mL), was slowly added 2.5 M n-butyllithium in hexanes (162 mL, 0.405 mol). The resulting solution was stirred at 0° C. for 2 hours and quenched with water. After stirring for an additional 0.5 hour, the reaction mixture was poured into ice-water and extracted with ethyl acetate. The organic layer was washed with water several times and dried over $MgSO_4$. Removal of solvent afforded a residue. This residue was taken up in acetonitrile (700 mL) and treated with potassium ferricyanide (198.0 g, 0.601 mol) aqueous solution (1110 mL) containing potassium hydroxide (99.0 g, 1.764 mol) for about 42 hours at room temperature. The mixture was extracted with ethyl acetate and dried over $MgSO_4$. After evaporation of the solvent, the crude product was purified by chromatography on silica gel (hexanes:ethyl acetate=10:1 as eluent) to afford 27.0 g (83%) of yellow powder.

Part B: Preparation of 9,9-dibutylacridan

To an ice-cooled solution of 9-butylacridine (27.0 g, 0.115 mol) and TMEDA (4.1 mL, 0.027 mol) in THF (135 mL), was added 2.5 M n-butyllithium in hexanes (140 mL, 0.350 mol) dropwise. The mixture was stirred at 0° C. overnight and quenched with water. After stirring for an additional 0.5 hours, the reaction mixture was poured into crushed ice and extracted with ethyl acetate. The organic solution was washed with water and dried over $MgSO_4$. The solvent was evaporated and the resulting residue was chromatographed on silica gel (hexanes:ethyl acetate=10:1 as eluent) to give 14.5 g (43%) of yellow powder.

MS, m/e (relative intensity): 293 ($M^+$, 1.8), 236 (100.0), 204 (5.4), 193 (37.1), 180 (5.6), 152 (0.9), 89 (0.2), 57 (0.6).

Part C: Preparation of
2,7-dibromo-9,9-dibutylacridan

To a stirred solution of 9,9-dibutylacridan (9.9 g, 34 mmol) in dichloromethane (300 mL), containing silica gel (Merck, grade 10180, 136 g), a solution of N-bromosuccinimide (NBS) (12.1 g, 68 mmol) in dichloromethane (400 mL) was added slowly. The reaction mixture was stirred overnight in the absence of light at room temperature. The silica gel was filtered off, the filtrate was concentrated under reduced pressure, and the residue was partitioned between ethyl acetate and water. The organic layer was dried over $MgSO_4$ and evaporated in vacuo. The crude product was chromatographed on silica gel (hexanes:ethyl acetate=9:1 as eluent) to give 8.7 g (57%) of greenish yellow powder.

Example 2

This Example describes a synthetic route to an acridan monomer, 2,7-dibromo-9,9-dibutyl-N-hexylacridan.

A mixture of 2,7-dibromo-9,9-dibutylacridan (8.7 g, 19.3 mmol), 1-bromohexane (6.4 g, 38.6 mmol), benzyltriethylammonium chloride (0.1 g, 1.1 mol %) and potassium hydroxide (2.2 g, 38.6 mmol) in DMSO (dimethylsulfoxide, 55 mL) was heated at 105° C. with stirring for 24 hours. The mixture was cooled to room temperature and poured into water. After extraction with ethyl acetate, the organic layer was washed with water and dried over MgSO$_4$. The solvent was evaporated in vacuo. The resulting residue was subjected to chromatography on silica gel (hexanes:ethyl acetate=9:1 as eluent) to give 10.0 g (97%) of brownish yellow powder.

Example 3

This Example describes a synthetic route to an acridan monomer, 2,7-dibromo-9,9-dibutyl-N-octylacridan.

In 50 mL flask, 2,7-dibromo-9,9-dibutylacridan (4.0 g, 8.9 mmol), 1-bromooctane (3.5 g, 18.0 mmol), and potassium hydroxide (1.0 g, 17.8 mmol) were mixed in DMSO (25 mL) and heated to 120° C. with stirring overnight. The resulting mixture was cooled and poured into water. Ethyl acetate was used to extract the product. The organic extract was washed with water and dried over MgSO$_4$. The solvent was removed under reduced pressure. The crude product was purified by column chromatography (silica gel, hexanes:ethyl acetate=9:1) to give a greenish yellow powder.

$^1$H-NMR (500 MHz, CDCl$_3$, ppm): δ 7.29 (s, 2H, aromatic protons), 7.23 (d, 2H, J 8.8 Hz, aromatic protons), 6.68 (d, 2H, J 8.8 Hz, aromatic protons), 3.69 (t, 2H, J 8.1 Hz,

1.71-1.80 (m, 6H, alkyl protons), 1.27-1.39 (m, 8H, alkyl protons), 1.13-1.18 (m, 6H, alkyl protons), 0.87-0.92 (m, 7H, alkyl protons), 0.73-0.76 (t, 6H, J 7.32 Hz, alkyl protons).

$^{13}$C-NMR (500 MHz, CDCl$_3$, ppm): δ 140.3, 130.1, 129.9, 129.6, 114.1, 112.7, 47.0, 45.4, 44.7, 32.2, 29.8, 29.7, 27.3, 27.1, 26.2, 23.4, 23.0, 14.5, 14.3.

Example 4

This Example describes a synthesis of a co-polymer, poly (9,9-di(2-ethylhexyl)fluorene-co-9,9-dibutyl-N-octylacridan) (a).

9,9-di(2-ethylhexyl)fluorene-2,7-bisboronicacid (0.913 g, 1.92 mmol), 2,7-dibromo-9,9-dibutyl-N-octylacridan (1.079 g, 1.92 mmol), benzyltriethylammonium chloride (0.078 g, 0.34 mmol) and tetrakis(triphenylphosphine)palladium (Pd (PPh$_3$)$_4$) (0.126 g, 0.11 mmol) were dissolved in a mixture of THF (10 mL) and 2 M potassium carbonate aqueous solution (10 mL). The resulting solution was put under a nitrogen atmosphere and refluxed with vigorous stirring over the weekend. After the reaction mixture was cooled down to room temperature, it was poured slowly into methanol with constant stirring. A greenish yellow fibrous solid was collected by filtration and dried under vacuum. The raw product was dissolved in THF (15 mL), filtered through a membrane filter with the pore size of 0.45 μm to remove undissolved particles, and precipitated from ethanol. This purification procedure of dissolution, micro-filtration and precipitation was repeated one more time to yield 510 mg of product.

$^1$H-NMR (500 MHz, CDCl$_3$, ppm): δ 7.79 (d, 2H, J=7.8 Hz, aromatic protons), 7.51-7.62 (m, 8H, aromatic protons), 7.00 (s, 2H, aromatic protons), 3.92 (br, 2H,

1.91-2.06 (m, 8H, alkyl protons), 1.16-1.57 (m, 16H, alkyl protons), 0.63-0.95 (m, 39H, alkyl protons).

Example 5

This Example describes the electrochemistry of poly(9,9-di(2-ethylhexyl)fluorine-co-9,9-dibutyl-N-octylacridan) and its energy levels of HOMO and LUMO The cyclic voltammetry measurements were carried out on BAS 100A Electrochemical Analyzer. A silver wire was used as quasi-reference electrode, platinum wire as auxiliary electrode and graphite as working electrode. The polymer was dissolved in chloroform and coated on the working electrode. All measurements were carried out in acetonitrile with tetra-n-butylammonium hexafluorophosphate (0.1 M) as supporting electrolyte under a nitrogen atmosphere at room temperature.

Figure 2:
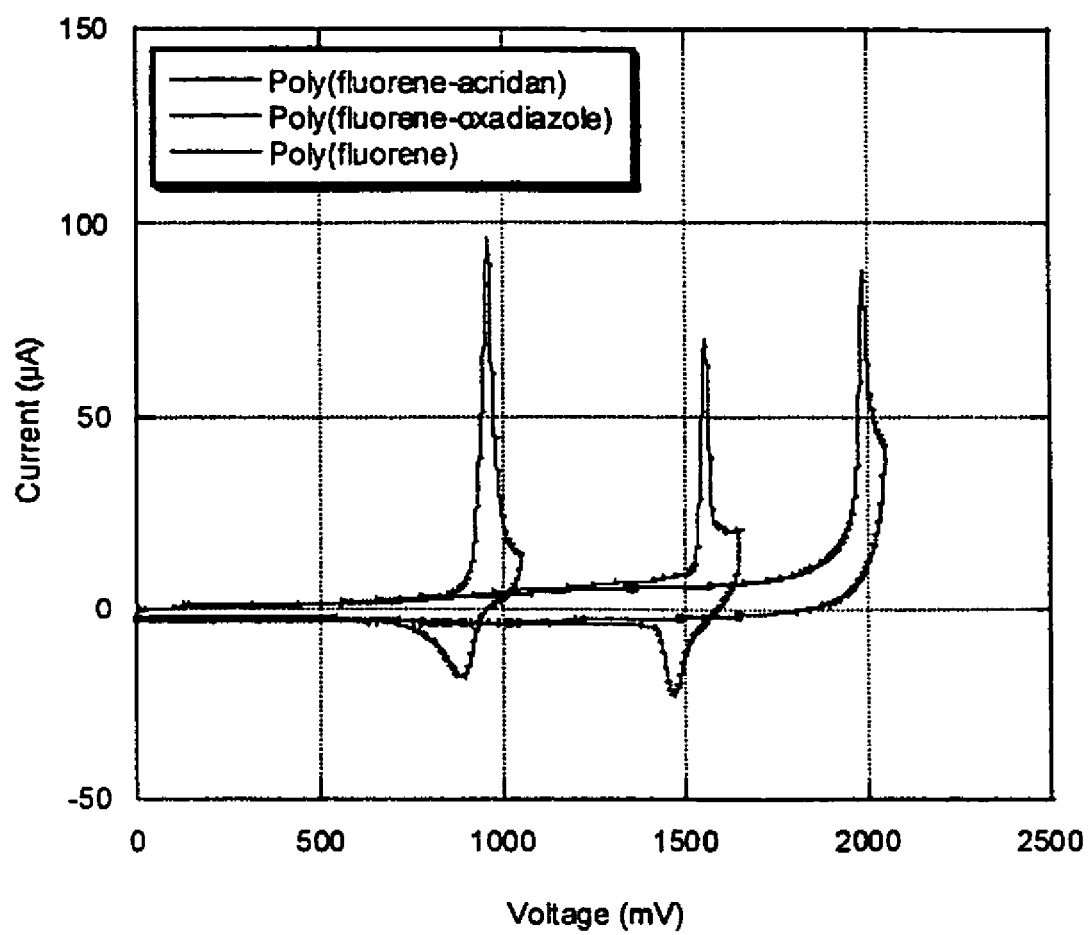
FIG. 2 compares cyclic voltammetry data between a poly(acridan-fluorene), poly(fluorene), and poly(fluorene-oxadiazole).

FIG. 2 depicts the cyclic voltammetry plot for the polymer set forth in Example 4, compared to the cyclic voltammetry of two other conjugated polymers, namely, poly(fluorine) and poly(fluorine-oxadiazole). The energy level of highest occupied molecular orbital (HOMO) was estimated to be 6.2, 5.8 and 5.3 eV for poly(9,9-di(2-ethylhexyl)fluorene-oxadiazole) (designated as poly(fluorene-oxadiazole)), poly(9,9-di (2-ethylhexyl)fluorene (designated as polyfluorene), and poly(fluorene-acridan) of Example 4, respectively. As the polymer of Example 4 has a lower HOMO energy level (relative to vacuum), it is much easier to inject hole from an electrode. Thus, this data demonstrates that acridan polymers described herein are good candidates for hole-transport materials.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment.

Conversely, various features that are, for brevity, described in the context of a single embodiment, may also be provided separately or in any subcombination. Further, reference to values stated in ranges include each and every value within that range.

The invention claimed is:

1. A compound having formula I:

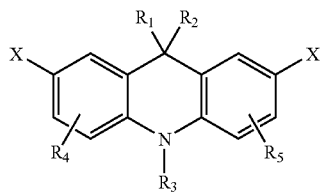

wherein:
R$_1$, R$_2$, R$_3$, R$_4$, and R$_5$ are each, independently, H, alkyl, alkenyl, alkynyl, heteroalkyl, heteroalkenyl, heteroalkynyl, tert-butyl benzyl or aryl, wherein at least one of R$_1$, R$_2$, R$_3$, R$_4$, and R$_5$ is other than H and is further substituted with halogen, amino, cyano, nitro, alkyl, alkoxy, alkylamino, or alkylthio; and X is, independently, Br, I, —COOH, or —C$_6$H$_4$—COOH.

2. A compound having formula I:

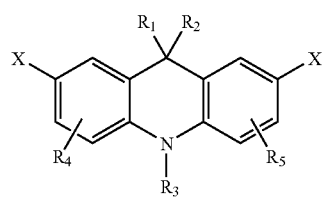

wherein R$_1$ and R$_2$ are both alkyl, and R$_3$, R$_4$, and R$_5$ are each, independently, H, alkyl, alkenyl, alkynyl, heteroalkyl, heteroalkenyl, heteroalkynyl, or aryl, and X is, independently, Br, I, —COOH, or —C$_6$H$_4$—COOH.

3. A compound having formula I:

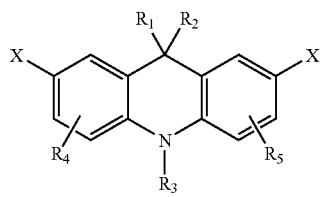

wherein R$_3$ is aryl, and R$_1$, R$_2$, R$_4$, and R$_5$ are each, independently, H, alkyl, alkenyl, alkynyl, heteroalkyl, heteroalkenyl, heteroalkynyl, or aryl, and X is, independently, Br, I, —COOH, or —C$_6$H$_4$—COOH.

4. A compound having formula I:

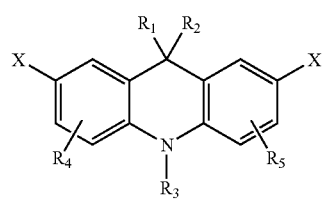

wherein R$_3$ is alkyl, and R$_1$, R$_2$, R$_4$, and R$_5$ are each, independently, H, alkyl, alkenyl, alkynyl, heteroalkyl, heteroalkenyl, heteroalkynyl, or aryl, and X is, independently, Br, I, —COOH, or —C$_6$H$_4$—COOH.

5. The compound of claim 2, wherein:
R$_1$ and R$_2$ is C$_4$H$_9$,
R$_3$ is H, C$_6$H$_{13}$, C$_8$H$_{17}$, or tert-butyl-benzyl,
R$_4$ and R$_5$ are H, and
X is Br.

* * * * *